United States Patent [19]

Cooper

[11] Patent Number: 4,900,668
[45] Date of Patent: Feb. 13, 1990

[54] PREPARATION OF PYRUVIC ACID

[75] Inventor: Brian Cooper, Mannheim, Fed. Rep. of Germany

[73] Assignee: BASF Aktiengesellschaft, Ludwigshafen, Fed. Rep. of Germany

[21] Appl. No.: 251,363

[22] Filed: Sep. 30, 1988

[30] Foreign Application Priority Data

Oct. 1, 1987 [DE] Fed. Rep. of Germany ....... 3733157

[51] Int. Cl.$^4$ .................. C12P 19/04; C12R 1/01; C07G 17/001; C07G 17/00
[52] U.S. Cl. .................................. 435/101; 435/822; 435/823; 536/114; 536/123
[58] Field of Search .................. 435/101, 822, 823; 536/114, 123

[56] References Cited

U.S. PATENT DOCUMENTS 4,514,563 4/1985 Fujiyama et al. .................. 536/114

OTHER PUBLICATIONS

Chemical Abstracts, 63:12285b, (1965).
Chemical Abstracts, 58:5737d, (1963).
Chemical Abstracts, 58:14463e, (1963).
Chemical Abstracts, 62:6832a, (1965).
Chemical Abstracts, 64:16312b, (1966).
Chemical Abstracts, 70:86273w, (1969).
Chemical Abstracts, 63:12285b, (1965).
Chemical Abstracts, 82:123305d, (1975).
Chemical Abstracts, 82:153737p, (1975).
Chemical Abstracts, 83:204815t, (1975).
Chemical Abstracts, 84:178212t, (1976).
Chemical Abstracts, 91:173387p, (1979).
Chemical Abstracts, 98:15498r, (1983).
Chemical Abstracts, 104:205568d, (1986).
Pritchard, *Journal of Experimental Botany*, vol. 16, (1965), pp. 487–497.
Takao et al., *Journal of Fermentation Technology*, vol. 60, No. 4, (1982), pp. 277–280.
Moriguchi, *Agricultural and Biological Chemistry*, vol. 46(4), (1982), pp. 955–961.
Harada et al., *Agricultural and Biological Chemistry*, vol. 46(11), (1982), pp. 2645–2658.
*Chemical Abstracts*, vol. 59, 13312, "Pyruvic Acid Fermentation by Bacteria", T. Saito, et al.

*Primary Examiner*—Ronald W. Griffin
*Assistant Examiner*—Pamela Webber
*Attorney, Agent, or Firm*—Oblon, Spivak, McClelland, Maier & Neustadt

[57] ABSTRACT

Pyruvic acid is prepared by microbiological oxidation of D-(−)-lactic acid.

9 Claims, No Drawings

PREPARATION OF PYRUVIC ACID

The present invention relates to a process for the preparation of pyruvic acid and its salts.

Pyruvic acid is a useful intermediate for chemical syntheses, for example for the preparation of drugs, crop protection agents, polymers and foods. It is therefore understandable that many attempts have been made to develop industrial production processes. Since pyruvic acid is an important metabolite in the metabolism of all microorganisms, it is not surprising that attention has been focused primarily on enzymatic and fermentation processes.

Many of the biotechnological preparation processes described aim at converting a suitable carbon source into pyruvic acid. It has long been known that various microorganisms can form pyruvic acid. For example, Biquet et al. (Chem. Abstr. 58 (1963), 14463 e) describe the formation of pyruvic acid by various fungal strains of the genus candida. A similar observation was made by Kretovich et al. with a strain of the fungus Candida Tropicalis (Chem. Abstr. 62 (1965), 6832 a). The use of a strain of the *Acetobacter suboxydans* species for the direct preparation of pyruvic acid from D-glucose was described by Abe and Seito (Chem. Abstr. 63 (1965), 12285 b). The use of fungal strains of the genus Mucor for the preparation of pyruvic acid from glucose is likewise known (J. Exptl. Botany 16 (1965) 487). The conversion of paraffins to pyruvic acid and 2-oxoglutaric acid with various Mycobacterium strains is mentioned (Chem. Abstr. 64 (1966), 16312 b). The use of a Corynebacterium strain for the preparation of pyruvic acid from D-gluconic acid has been described (Chem. Abstr. 70 (1969), 86273 w). The conversion of short-chain fatty acids into pyruvic acid by various strains of the genera Nocardia, Arthrobacter, Brevibacterium, Corynebacterium, Mycobacterium or Candida has been described by Maeyashiki and Okada (Chem. Abstr. 82 (1975), 123305 d). A similar discovery using short-chain fatty amides with strains of the same genera has been reported (Chem. Abstr. 82 (1975), 153737 p). A process for the preparation of pyruvic acid from D-gluconic acid with the strains *Nocardia fumifera* and *Pseudomonas tabati* was described by Uchio and Hirose (Chem. Abstr. 83 (1975), 204815 t). A process for the preparation of pyruvic acid from D-glucose with a *Candida lipolytica* mutant requiring thiamine and L-methionine was reported by Uchio et al. (Chem. Abstr. 84 (1976), 178212 t). A process for the preparation of pyruvic acid from glycerol with a strain of the genus *Xanthomonas campestris* has been described by Behrens and Fiedler (East German Pat. No. 135,213 (1979)). The conversion of citrus fruit peel wastes into pyruvic acid with the aid of the fungus *Debaryomyces coudertii* has been described by Moriguchi (Agric. Biol. Chem. 46 (1982), 955). Tacao and Tanida (J. Ferment. Technol. 60 (1982), 277) reported that the formation of pyruvic acid from D-glucose with the aid of the Basidiomycetes Schizophyllum commune. A process for the preparation of pyruvic acid from D-glucose with *Agaricus campestris* has been described by Takao (Chem. Abstr. 98 (1983), 15498 r). Izumi and Matsumura described Acinetobacter strains which convert 1,2-propanediol into pyruvic acid (Agric. Biol. Chem. 46 (1982), 2653). The conversion of tartaric acid to pyruvate by *Pseudomonas putida* has been described by Miyata et al. (Chem. Abstr. 104 (1986), 205568 d).

However, all these microorganisms are either unavailable to the general public or are not very suitable for industrial production, since they form pyruvic acid in only low concentration or poor yield, frequently in addition to one or more other acids. Economical preparation is therefore impossible.

It has also been stated that racemic lactic acid can be converted into pyruvic acid by oxidation with the aid of microorganisms. Abe and Saito (Chem. Abstr. 58 (1963), 5737 d and (1963), 6760) describe the use of various bacterial strains, which are not available to the general public, for the oxidation of racemic lactic acid. However, these strains are not very suitable for the preparation of pyruvic acid since they form the desired product in insufficient yield (from 27 to 52%). Moreover, considerable amounts of glucose, peptone and meat extract are required in order to produce the cell mass necessary for the reaction. Such expensive components of the medium prevent economical production of the pyruvic acid.

No industrial process for the production of pyruvic acid has been described to date.

There was therefore a need for economical, industrially feasible process for the preparation of pyruvic acid.

We have found a microorganism which is capable of converting optically pure D-(−)-lactic acid quantitatively into pyruvic acid with a high space-time yield in a cheap nutrient medium.

The present invention relates to a process for the preparation of pyruvic acid and its salts, wherein the bacterium Acetobacter spec. ATCC 21409 is cultivated under aerobic conditions in the presence of D-(−)-lactic acid.

D-(−)-lactic acid can readily be prepared from glucose in a known manner.

Acetobacter spec. ATCC 21409 has been deposited at the American Type Culture Collection (ATCC), Rockeville, Md., USA, and is freely available.

To carry out the novel process, the strain Acetobacter spec. ATCC 21409 is innoculated onto a nutrient medium containing D-(−)-lactic acid and incubated therein. The fermentation can be carried out continuously or batchwise.

The cells of the strain are allowed to act directly on the substrate. Any known incubation method can be employed, the use of fermenters in the form of deep, aerated and stirred tanks being particularly preferred. Very good results are obtained by using a liquid nutrient medium.

The choice of the nutrient medium for cultivating the microorganism is not critical, but particularly economical components of the medium should be used in order to achieve greater cost-efficiency. Suitable nutrient media are those which contain carbon sources, nitrogen sources, inorganic salts and, if required, small amounts of trace elements and vitamins. Suitable nitrogen sources are inorganic or organic nitrogen compounds or materials which contain these compounds. Examples are ammonium salts, corn steep liquor, autolyzed brewer's yeast, hydrolyzed soybean meal, wheat gluten, yeast extract, yeast, urea and potato protein. The use of corn steep liquor is particularly advantageous. Suitable carbon sources are sugars, such as D-glucose, mannose or galactose, polyalcohols, such as mannitol, and alcohols, such as ethanol.

Examples of inorganic salts are the salts of calcium, magnesium, manganese, potassium, zinc, copper, iron and other metals. The phosphate ion may be mentioned in particular as an anion of the salts. If necessary, growth factors, e.g. pantothenic acid, p-aminobenzoic acid and thiamine, are added to the nutrient medium. The mixing ratio of the stated nutrients depends on the method of fermentation and is determined from case to case.

In general, D-(−)-lactic acid concentrations of about 1–100, preferably about 10–50, g/l are suitable for carrying out the novel process.

The cultivation conditions are specified so that the best possible yields are obtained. Preferred cultivation temperatures are from 24° to 32° C., preferably 26° to 30° C. The pH is from 5 to 8, preferably from 6 to 8. In general, an incubation time of from 4 to 48 hours is sufficient. Within this time, the maximum amount of the desired product accumulates in the medium. It is advisable to monitor the amounts of pyruvic acid forming in the incubation medium and to terminate the reaction when the amount of pyruvic acid has reached the maximum.

Suffficient aeration must be ensured, since the reaction takes place at high velocity and yield only if sufficient oxygen is applied.

The required amount of D-(−)-lactic acid can be added to the medium all at once at the beginning or a little at a time during cultivation.

The D-(−)-lactic acid mentioned as a substrate is introduced in the form of a salt into the nutrient medium. For example, the sodium potassium, ammonium and calcium salts of D-(−)-lactic acid can be used. The calcium salt is particularly advantageously employed.

The pyruvic acid formed and precipitated into the medium can be quantified by known methods. Enzymatic detection methods are advantageous for this purpose. The pyruvic acid and its salts can be isolated and purified by known processes. For example, basic ion exchangers are suitable for this purpose. Alternatively, the fermentation liquor can be evaporated down under reduced pressure and the product crystallized at room temperature. The crystal thus produced can be isolated by centrifuging and can be dried.

Where the pyruvic acid is to be further used without being worked up, it is sufficient to destroy the cells of the microorganism Acetobacter spec. ATCC 21409 in the reaction mixture in order to prevent further conversion of the product. This can be done, for example, by adding 0.1% of n-octanol and heating at 45° C. for 30 minutes. Alternatively, the fermentation liquor can be freed from the microorganism using commercial sterile filters. Such fermentation liquors should be protected from microbial contamination by suitable measures, for example by cooling.

The Examples which follow illustrate the invention.

EXAMPLE 1

Preparation of a Stock Culture

A solid nutrient medium (medium A) which contained the following components was prepared:

| | |
|---|---|
| D-(−)-mannitol | 10 g/l |
| Ammonium sulfate | 5 g/l |
| Magnesium sulfate 7 hydrate | 0.5 g/l |
| Manganese sulfate 1 hydrate | 0.05 g/l |
| Yeast extract | 0.05 g/l |
| Peptone | 0.05 g/l |
| Potassium dihydrogen phosphate | 1.5 g/l |
| Dipotassium hydrogen phosphate | 3.6 g/l |
| Agar | 20 g/l |

| -continued | |
|---|---|
| Water to | 1 l. |

The phosphate salts are sterilized separately from the remaining medium (for 20 minutes at 121° C.), cooled and then added. The pH of the medium was 7.

Cells of the microorganism Acetobacter spec. ATCC 21409 were subjected to decimal dilution and plated out on the solid nutrient medium. After incubation for 48 hours at 28° C., individual colonies appeared at the appropriate dilution. Individual clones were removed and were each inoculated into 20 ml of preculture nutrient medium (=medium B) in sterile 100 ml conical flasks:

| | |
|---|---|
| D-(−)-mannitol | 10 g/l |
| Yeast extract | 5 g/l |
| Magnesium sulfate 7 hydrate | 0.5 g/l |
| Water to | 1 l. |

The pH was not regulated and sterilization was carried out for 20 minutes at 121° C.

Incubation of this preculture was effected at 28° C. in a commercial shaking incubator at 250 rpm for 16 hours.

To check the biotransformation efficiency, 20 ml portions of medium C were introduced into sterile 100 ml conical flasks closed with wadding.

| Medium C: | |
|---|---|
| D-(−)-mannitol | 10 g/l |
| Corn steep liquor | 40 g/l |
| D-(-)-lactic acid (calcium salt) | 10 g/l (calculated as free acid) | pH 7 with 5M NaOH.

Sterilization at 121° C. for 40 minutes.

2 ml of each of the precultures were innoculated onto this medium. The batches were incubated in a shaking incubator at 28° C. and 250 rpm. The concentrations of D-(−)-lactic acid and pyruvic acid were determined using commercial enzymatic test sets. As a rule, 100% of the D-lactate used had been converted after 5 hours. The concentration of pyruvic acid was not less than 10 g/l. A colony having this efficiency was further cultivated and was lyophilized in a conventional manner. This material served as innoculation material for all further experiments.

EXAMPLE 2

Fermentation in Shaking Flasks 100 ml of medium C were introduced into a 1000 ml conical flask closed with wadding and was sterilized. 100 ml of the same nutrient medium, but with 10 g/l of L-(+)-lactic acid (sodium salt, calculated as acid), were prepared as a control. Both cultures were inoculated with 10 ml of a preculture, as described in Example 1. Incubation was effected at 28° C. and 250 rpm in a shaking incubator. Samples were taken at 60 minute intervals and the content of pyruvic acid determined. The result is shown in the Table below. Pyruvic acid concentration (g/l)

| Time (hours) | Batch with added D-lactate | Batch with added L-lactate |
| --- | --- | --- |
| 0.0 | 0.0 | 0.0 |
| 1.0 | 1.2 | 0.8 |
| 2.0 | 3.0 | 1.4 |
| 3.0 | 5.7 | 1.2 |
| 4.0 | 10.2 | 0.9 |
| 5.0 | 11.4 | 0.7 |

Analysis of the fermentation liquors after 5 hours showed that the D-(−)-lactic acid had been completely converted. On the other hand, all of the L-(+)-lactic acid was still present. The pyruvic acid formed in this batch is produced by the oxidation of the D-lactic acid introduced with the corn steep liquor. This also explains the somewhat excessively high concentration of pyruvic acid in the batch with D-(−)-lactic acid.

EXAMPLE 3

Formation of Pyruvic acid in a Fermenter

A 1 liter fermenter was charged with 900 ml of medium C, containing 20 g/l of D-lactic acid (calcium salt), and was sterilized. The preculture used comprised 100 ml of a 12 hour old culture of the strain Acetobacter spec. ATCC 21409 on medium B, the preparation of which has been described in Example 1. Fermentation was effected at 28° C., an aeration rate of 0.5 vvm and a stirrer speed of 1,000 rpm. No antifoam was added.

After 9 hours, the concentration of pyruvic acid (enzymatically determined) was 19.6 g/l.

I claim:

1. A process for the preparation of pyruvic acid and its salts, comprising the steps of:
   cultivating the bacterium Acetobacter spec. ATCC 21409 under aerobic conditions in the presence of D-(−)-lactic acid, and
   isolating the pyruvic acid and its salts.
2. The process of claim 1, wherein said lactic acid is an aqueous lactic acid solution having a concentration of about 1–100 g/l.
3. The process of claim 2, wherein said lactic acid solution has a concentration of 10–50 g/l.
4. The process of claim 1, wherein said cultivating step is conducted at a temperature from 24°–32° C.
5. The process of claim 4, wherein said cultivating step is conducted at a temperature of 26°–30° C.
6. The process of claim 1, wherein said cultivating step is conducted at a pH from 5–8.
7. The process of claim 6, wherein said cultivating step is conducted at a pH from 6–8.
8. The process of claim 1, wherein said lactic acid is in the form of a salt selected from the group consisting of the sodium, potassium, ammonium and calcium salts of D-(−)-lactic acid.
9. The process of claim 8, wherein said salt is the calcium salt of D-(−)-lactic acid.

* * * * *

UNITED STATES PATENT AND TRADEMARK OFFICE
CERTIFICATE OF CORRECTION

PATENT NO. : 4,900,668

DATED : Feb. 13, 1990

INVENTOR(S) : Bryan Cooper

It is certified that error appears in the above-identified patent and that said Letters Patent is hereby corrected as shown below:

On the title page:

The inventor's name is incorrectly spelled, "Brian Cooper" should be:

--Bryan Cooper--

Signed and Sealed this

Ninth Day of April, 1991

Attest:

HARRY F. MANBECK, JR.

*Attesting Officer*     *Commissioner of Patents and Trademarks*